United States Patent
Glaser et al.

(10) Patent No.: US 6,229,047 B1
(45) Date of Patent: May 8, 2001

(54) DIPOLE ALIGNED NLO CHROMOPHORES

(75) Inventors: Ranier E. Glaser; Grace S. Chen, both of Columbia, MO (US)

(73) Assignee: The Curators of the University of Missouri

(*) Notice: Subject to any disclaimer, the term of this patent is extended or adjusted under 35 U.S.C. 154(b) by 0 days.

(21) Appl. No.: 08/567,070

(22) Filed: Dec. 4, 1995

(51) Int. Cl.$^7$ ............................................. C07C 251/24
(52) U.S. Cl. ..................... 564/249; 252/582; 252/589; 359/326; 359/328; 372/20; 372/21; 372/22; 546/231; 558/422; 560/34; 562/439
(58) Field of Search ..................... 564/249; 252/582, 252/589; 359/326, 328; 372/20, 21, 22; 546/231; 558/422; 560/34; 562/439

(56) References Cited

U.S. PATENT DOCUMENTS

| | | | |
|---|---|---|---|
| 4,810,338 | 3/1989 | DeMartino et al. | 204/157.88 |
| 5,163,060 | 11/1992 | Mitra et al. | 372/21 |
| 5,204,178 | 4/1993 | Licht et al. | 428/333 |
| 5,224,196 | 6/1993 | Khanarian et al. | 385/122 |
| 5,401,612 | 3/1995 | Etzbach et al. | 430/285 |

OTHER PUBLICATIONS

Houlton et al., "Molecular Materials Containing Donor and Acceptor Groups, etc." J. Chem. Soc. Dalton Trans., pp. 2235–2241, 1992.*

Kawabe et al. Second–order Nonlinear Optical Properties of New Organic Conjugated Molecules, J. Mater. Chem. (1992), 2(10), 1025–31, abstracted in Chem. Abst. 118:29481, 1993.*

Kadry et al. "1, 3, 5, 7–Tetraazablcyclo[3.3.0]octane–2, 6–dithiones: Synthesis and Lack of Antimicrobial activity," Sulfur Lett. (1990), 10(5), 205–9, abstracted in Chem Abst. 113:40502, 1990.*

Appenroth, "Thermochromism and Photochromism of Aryl–Substituted Acyclic Azines; IX. Fluoreswoence Studies," Z. Chem. (1988), 26(3), 106–7, abstracted in Chem Abst. 105:180627, 1986.*

Chen et al, Stereochemistry and Stereoelectronics of Azines. A Solid State Study of Symmetrical, (E,E)–Configured, Para–Substituted (H, F, Cl, Br, CN) Acetophenone Azines, *The Journal of Organic Chemistry*, 59 (1994).

Chen, et al, Polymorphism and C=N—N=C Conformational Isomers of Azines: X–ray Crystal and Ab Initio Structures of Two Rotational Isomers of Methyl (para–Tolyl) Ketone Azine, "Stereochemistry and Stereoelectronics of Azines, Part 3," *Angwandte Chemie* (English Reprint 1994/33), Angew, Chem. Int. Ed. Engl., vol. 33, No. 10 (1994).

Glaser et al, Comparative analysis of crystal structures of E,E–configured para–substituted acetophenone azines with halogen, oxygen, nitrogen and carbon functional groups, *J. Chem. Soc. Trans. 2*, pp. 1449–1458 (1995).

Eaton, D.F., Nonlinear Optical Material, *Articles Science*, vol. 253, pp. 281–287 (Jul. 1991).

Williams, D.J., Organic Polymeric and Non–Polymeric Materials with Large Optical Nonlinearities, *Agnew. Chem. Int. Ed. Engl.*, vol. 23, pp. 690–703 (1984).

Long, N.J., Organometallic Compounds for Nonlinear Optics—The Search for En–light–enment!, *Agnew. Chem. Int. Ed. Engl.*, vol. 34, pp. 21–38 (1995).

* cited by examiner

Primary Examiner—Peter O'Sullivan
(74) Attorney, Agent, or Firm—William D. Jackson; Locke Liddell & Sapp LLP (57) ABSTRACT

A nonlinear optical material which is characterized as having a relatively high macroscopic dipole moment achieved through the generally parallel packing of dipolar molecules in a relative orientation to reinforce their dipole moments. The nonlinear optical material may be a crystalline azine or imine bridged di-arene in which the arenyl groups, which can be the same or different, are substituted with an electron donor group on the first arenyl group $Ar_1$ and A is an electron acceptor group which is substituted on the second arenyl group $Ar_2$. B is an azine or imine bridge which extends between and interconnects the first and second arenyl groups. The nonlinear optical material has a dipole alignment factor of at least 0.1, more preferably, at least 0.5. A more specific nonlinear optical material is a crystalline azine bridged di-arene having a net macroscopic dipole moment and characterized by the formula:

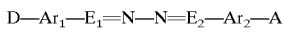

$$D-Ar_1-E_1=N-N=E_2-Ar_2-A$$

Here, $Ar_1$ and $Ar_2$ are arenyl groups which may be the same or different and are selected from the group consisting of mononuclear aryl groups and conjugated dinuclear aryl groups. D and A are electron donor and electron acceptor substituents, respectively and $E_1$ and $E_2$ are each independently substituted or unsubstituted methylene or ethylene groups which may be the same or different and which can have substituent side groups which contain 1 or 2 carbon atoms and which can be racemically configured.

23 Claims, 5 Drawing Sheets

Molecule A

Molecule B

DIPOLE ALIGNED NLO CHROMOPHORES

FIELD OF THE INVENTION

This invention relates to nonlinear optical materials and more particularly, crystalline nonlinear optical materials provided by the parallel crystal packing of asymmetrical molecules exhibiting dipole moments.

BACKGROUND OF THE INVENTION

The alignment of symmetrical molecules can be achieved through a crystal packing relationship so long as the molecules are symmetrical. For example, Chen et al, *Stereochemistry and Stereoelectronics of Azines. A Solid State Study of Symmetrical, (E,E)-Configured, Para-Substituted (H, F, Cl, Br, CN) Acetophenone Azines, The Journal of Organic Chemistry*, 59 (1994) (hereinafter Chen I) and Chen et al, *Polymorphism and C=N—N=C Conformational Isomers of Azines: X-ray Crystal and Ab Initio Structures of Two Rotational Isomers of Methyl (para-Tolyl) Ketone Azine*, "Stereochemistry and Stereoelectronics of Azines, Part 3", *Angwandte Chemie* (English Reprint 1994/33), Angew, Chem. Int. Ed. Engl., Vol. 33, No. 10 (1994) (hereinafter Chen II), disclose the stereochemical configurations of para-disubstituted symmetrical acetophenone azines and various crystal packing schemes associated with these symmetrical molecules. In Chen I, five symmetrical acetophenone azines are disclosed. These include the basic substituted compound, 1,4-diphenyl-1,4-dimethyl-2,3-diazabutadiene, and the corresponding di-fluoro, di-chloro, di-bromo and di-cyano compounds with the functional substituents in each case in the para position with respect to the azinyl bridge. Chen II discloses the corresponding di-methyl compound, the methyl groups again being in the para position.

Chen I discusses crystallographic data and crystal packing effects for the five compounds disclosed there. The unsubstituted and di-fluoro, di-chloro and di-cyano phenyladiene azines all exhibit monoclinic symmetry while the di-bromo structure has orthorhombic symmetry. As disclosed in Chen II, the unsubstituted compound and the di-halo substituted compounds all exhibited gauche conformation with torsion angles that decrease with the increasing electronegativity of the halogen substituents. The di-cyano compound is described as being in a trans N—N conformation in which the torsion angle is 180°, notwithstanding an electronegativity of the cyano group between the values for chlorine and bromine.

The crystal structures and packing configurations of additional para-disubstituted symmetrical azines are disclosed in Glaser et al, *Comparative analysis of crystal structures of E,E-configured para-substituted acetophenone azines with halogen, oxygen, nitrogen and carbon functional groups*, J. Chem. Soc. Trans. 2, pp. 1449–1458 (1995). Here, the solid state structures of fifteen para-disubstituted azines, including those disclosed in Chen I and Chen II are examined. Additional substituent groups, in addition to those discussed in the Chen et al publications include amino and alkylamino groups, ethers and fluorinated ethers, esters, nitro groups and amide groups.

In contrast to the symmetrical molecules disclosed in the aforementioned Chen et al and Glaser et al papers, asymmetrical molecules can be employed to produce materials showing non-linear optical (NLO) effects. These materials include aromatic materials either bridged or unbridged which are substituted with electron donor and electron acceptor substituents. For example, Eaton, D. F., *Nonlinear Optical Materials, Articles Science*, Vol. 253, pp. 281–287 (July 1991) discloses second order NLO materials based on organic derivatives such as 4-Bromo-4'-methoxychalcone (BMC) and 3-Methyl-4-methoxy-4'-nitrostilbene (MMONS), the latter said to have a high second harmonic generation (SHG) value. Similar such materials are disclosed in Williams, D. J., *Organic Polymeric and Non-Polymeric Materials with Large Optical Nonlinearities, Agnew. Chem. Int. Ed. Engl.*, Vol 23, pp. 690–703 (1984) which discloses aromatic groups substituted with electron acceptor and electron donor groups which may be in the ortho-, meta- or para position as well as bridged structures in which the bridges take the form of ethylene or polyethylene bridges or aminoethylene bridges. Somewhat similar bridged materials are disclosed in Long, N. J., *Organometallic Compounds for Nonlinear Optics—The Search for En-light-enment!, Agnew. Chem. Int. Ed. Engl.*, Vol 34, pp. 21–38 (1995) in which the bridges may take the form of silane or polysilane groups as well as polygermanes and various metallocene compounds.

The difficulty with such materials heretofore has been that the materials having molecular dipole moments have been thought to invariably orient in their crystalline structures in a manner so as to produce little or no macroscopic dipole moments. In view of the difficulties encountered with either organic or inorganic crystalline materials, it has been proposed to form electric field aligned NLO chromophores in polymeric materials. Such polymeric materials are configured with spaced electron donor-electron acceptor groups in polymeric matrices which can be "poled" by an applied electrical field in order to align the polar electron donor acceptor groups in a manner to impart macroscopic NLO properties to the polymer. By way of example, U.S. Pat. No. 4,810,338 to DeMartino et al discloses liquid crystalline NLO polymers in which a polymer mainchain, such as polyvinyl acrylate, supports side chain connected electron donating or electron withdrawing groups. Suitable electron donor groups disclosed in DeMartino are amino, alkyl, alkoxy, alkylthio, hydroxy, thiolo, acyloxy, vinyl, halo and the like. Suitable electron-withdrawing substituents include nitro, haloalkyl, cyano, acyl, alkanoyloxy, alkoxysulfonyl, and the like. A macroscopic dipole moment can be imparted to the polymer structure by means of a "poling" procedure in which an electric field is applied to induce a nonconcentrosymmetric orientation of the side chain NLO moieties. As disclosed in DeMartino, the liquid crystalline polymer melt is disposed within a "poling" cell in an applied electrical field is maintained for a 24 hour period in which the polymer is cooled to obtain the noncentrosymmetrically oriented polymer matrix. The non-linear optical moieties are said to be aligned parallel to the direction of the electric field.

Other polymer structures having NLO side chains are disclosed in U.S. Pat. No. 5,224,196 to Chanarian et al. Here, non-linear optical moieties incorporated into the polymer matrix include various electron donor and electron acceptor groups linked via conjugated units such as azol linked or alkylene linked spacer groups. As disclosed here and also in U.S. Pat. No. 5,204,178 to Licht and U.S. Pat. No. 5,401,612 to Etzbach et al which disclose polyesters or other polymers containing NLO chromophores, the polymers can be subjected to a poling operation in order to arrive at macroscopic dipole moments.

SUMMARY OF THE INVENTION

In accordance with the present invention, there is provided nonlinear optical material which is characterized as having a relatively high macroscopic dipole moment achieved through the generally parallel packing of dipolar molecules in a relative orientation to reinforce their dipole moments. Preferably, the nonlinear optical material of the present invention is a crystalline azine bridged di-arene characterized by the formula:

$$D\text{—}Ar_1\text{—}B\text{—}Ar_2\text{—}A \quad (1)$$

In the above formula, $Ar_1$ and $Ar_2$ are arenyl groups which can be the same or different. D is an electron donor group which is substituted on the first arenyl group $Ar_1$ and A is an electron acceptor group which is substituted on the second arenyl group $Ar_2$. B is an azine or imine bridge which extends between and interconnects the first and second arenyl groups. Preferably, the nonlinear optical material of the present invention has a dipole alignment factor of at least 0.1. More preferably, the dipole alignment factor is at least 0.5.

In a further embodiment of the present invention, there is provided a crystalline azine bridged di-arene having a net macroscopic dipole moment and characterized by the formula:

$$D\text{—}Ar_1\text{—}E_1\text{=}N\text{—}N\text{=}E_2\text{—}Ar_2\text{—}A \quad (2)$$

Here, $Ar_1$ and $Ar_2$ are arenyl groups which may be the same or different and are selected from the group consisting of mononuclear aryl groups and other conjugated dinuclear aryl groups. D and A are electron donor and electron acceptor substituents, respectively and $E_1$ and $E_2$ are each independently substituted or unsubstituted methylene or ethylene groups which may be the same or different. Groups $E_1$ and $E_2$ can each have substituent side groups which contain 1 or 2 carbon atoms. Preferably, $Ar_1$ and $Ar_2$ are phenyl groups and $E_1$ and $E_2$ are each methylene groups with racemically configured methyl substituents. In yet a further embodiment of the invention, D is an electron donor selected from the group consisting of ethers, thioethers, amines, alkylamines, dialkylamines, and piperidines, including derivatives such as morpholine, and A is an electron acceptor selected from the group consisting of halo groups, nitro groups, cyano groups, carboxyl groups, carbonyl groups, and alkoxy carbonyl groups.

DETAILED DESCRIPTION OF THE INVENTION

As indicated by the aforementioned patents to DeMartino and Chanarian, in order for a material to function with NLO characteristics, the molecules of the material incorporating electron donor and electron acceptor units must be oriented with the acceptor units predominately oriented in one direction and the donor units predominately oriented in the other direction. While this can be achieved employing polymeric matrices in which NLO chromophores are aligned such as in poling by an applied electric field, has heretofore been thought to be difficult to meet this criterion for crystalline materials since the electrostatic forces on individual polar molecules tend to align the molecules in an end-to-end or antiparallel configuration such that the individual electrical dipoles tend to cancel one another as indicated below.

Various alignments of electrical dipoles can be demonstrated by reference to the following diagrams in which a dipolar molecule is indicated by the symbol ●→. In this convention, one end of the dipole, e.g. an electron donor, is indicated by → and the opposed polarity, e.g. the electron acceptor, end is indicated by the convention ●. When the dipole indicated by ●→ is viewed along a plane line 90° to the plane of the dipole, the electron donor end of the dipole → is indicated by the convention x̂ and the acceptor end of the dipole ● is indicated by the convention ●.

As shown in the following diagrams, several strings of dipoles are indicated as lying in the plane of the paper on the left-hand side of each diagram and a corresponding view for a plane which is 90° to the plane of the paper is indicated on the right-hand side of the diagram. Diagram ($D_1$) indicates a configuration have fully antiparallel aligned strings of dipoles. When a string of dipoles is considered in isolation, they will necessarily be aligned in a dipole reinforcing configuration such as shown by each of strings $S_1$, $S_2$ and $S_3$ in diagram $D_1$. The strings, however, are configured in relation to one another so that adjacent strings are aligned in opposite directions in the plane of the paper and this same configuration holds true for the adjacent set of strings in adjacent planes, parallel to the plane of the paper as shown on the right-hand side of the diagram. Diagram $D_1$ can be characterized as illustrating a fully anti-parallel alignment of dipoles.

Diagram $D_2$ shows an alignment which can be characterized as a semi-parallel alignment in which the strings when considered in a three dimensional context are 50% in parallel alignment and 50% in anti-parallel alignment. Thus, as shown on the left-hand side of diagram $D_2$, all of the strings in a given plane of symmetry are aligned in the same direction. However, the strings in adjacent planes parallel to the plane of the paper, while within that plane aligned in the same direction, are as a group aligned in the opposed direction to the alignment of the strings in the plane of the paper.

Finally, Diagram $D_3$ shows a fully parallel alignment of strings. Here, as illustrated, the dipoles in a given plane of symmetry (the plane of the paper), are aligned in the same direction and parallel planes above and below the plane of the paper, likewise exhibit parallel aligned strings of dipoles again in the same direction. In theory, this would result in a macroscopic dipole alignment factor $A_d$, discussed below for the NLO material of unity, e.g. for a crystalline material, $\mu_{cryst} = \Sigma \mu_{mol}$. In practice the 4-methoxy-4'-bromoacetophenone azine, which exhibits very good parallel alignment in the crystal form has thus far been crystallized from solution to have a value for $A_d$ of about 0.7. The dipole alignment factor may be designated by the relationship.

$$A_d = \frac{\mu_{mac}}{\Sigma \mu_{mol}}.$$

Here, $\mu_{mac}$ is the macroscopic dipole of the NLO material, which in the case of a crystal is expressed by the term, $\mu_{cryst}$, and $\Sigma \mu_{mol}$ is the sum of the molecular dipoles.

Ideally, if all of the molecules of a nonlinear optical material were to be aligned in a dipole reinforcing manner so that all of the molecular dipoles were exactly parallel and reinforcing, then the macroscopic dipole for the crystal $\mu_{cryst}$ would be equal or nearly equal to the sum of the microscopic molecular dipoles ($\mu_{mol}$) That is, $\mu_{mac} = \Sigma \mu_{mol}$ or in the case of a crystalline material, $\mu_{cryst} = \Sigma \mu_{mol}$. While the use of electric field aligned chromophores in polymeric matrices such as disclosed in the patents to DeMartino and Chanarian would permit this objective to be partially achieved, the ultimate result is still well below what might be desired. In addition, the polymeric matrix which acts as a carrier for the chromophores but does not in itself provide NLO activity, severely limits the achievable chromophore density, $D_c$ which can be defined in terms of the number of individual chromophores per unit volume NLO material.

The present invention involves a nonlinear optical material having a substantial net macroscopic dipole moment provided by a generally parallel alignment of asymmetric molecular systems having an azine or imine bridge interconnecting donor and acceptor substituted arenyl groups. The present invention can achieve linear crystal packing of the type achieved with the symmetrical molecules disclosed in the aforementioned Chen et al and Glaser et al articles, but can do so with asymmetric molecules having opposed donor and acceptor groups. That is, the parallel crystal packing configuration is achieved even though the molecules are not symmetrical and have electrical dipole moments. This is contrary to what one might expect based upon the previously developed data for the symmetrical molecules of the type disclosed in the aforementioned Chen et al papers. As noted there, the symmetrical cyano system exhibited a N—N trans conformation whereas the di-fluorinyl, -chloro and -bromo substituted molecules showed gauche conformations of torsional angles which tended to decrease with increasing electronegativity of the substituent groups. While one skilled in the art might in the absence of evidence to the contrary, expect the enhanced conjugation resulting from asymmetrical donor-acceptor substituents to result in reduced torsional angles, this does not occur. Instead, the asymmetrical azine compounds of the present invention exhibit gauche conformations which are of the same magnitude as the torsional angles of the corresponding symmetrical azines. This can be demonstrated by the x-ray diffraction data discussed below including the phenyl twist angles of various symmetrical and asymmetrical molecules.

The asymmetrical azines of the present invention can be prepared by reaction routes which can be analgized in some fashion to those followed in preparation of the symmetrical compounds disclosed in the aforementioned articles by Chen et al and Glaser et al but with appropriate modification in accordance with the present invention to accommodate asymmetrically substituted donor acceptor compounds. One suitable reaction route involves the reaction of appropriately substituted phenyl carbonyls to produce bridged azine compounds. By way of example, 4-methoxyacetophenone (diethoxyphosphinyl)hydrazone may be reacted with 4-para bromoacetophenone to produce the asymmetrical, 4-methoxy-4'-bromoacetophenone azine.

In experimental work involving the preparation of the bromo-methoxy substituted azine, diethyl phosphorohydrazidate was prepared by reaction of diethyl phosphite and hydrazine hydrate in accordance with the following protocol. Hydrazine hydrate (0.13 mol) was added dropwise to a stirred mixture of $CCl_4$ (40 $cm^3$), $CH_2Cl_2$ (70 $cm^3$), anhydrous $K_2CO_3$ (0.10 mol ) and triethylbenzylammonium chloride (0.66 mmol). The addition was carried out at 20–25° C., and the solution was stirred for 15 min at room temperature. A solution of diethyl phosphite (66 mmol) in $Ch_2Cl_2$ (10 $cm^3$) was then added at 20–30° C with external cooling and the was continued for 6 hours. The $K_2CO_3$ crystals were filtered off and rinsed with $CH_2Cl_2$. After removal of the solvents, the residue was kept under 0.5 Torr for 4 hours to remove volatile impurities. Product purity was verified by NMR spectroscopy. The diethyl phosphorohydrazidate was reacted with 4-methoxyacetophenone (to produce 4-methoxyacetophenone (diethoxyphosphinyl) hydrazone in accordance with the following protocol. A mixture of diethyl phosphorohydrazidate (0.62 mol), 4-methoxyacetophenone (0.062 mol) and benzene (45 $cm^3$) was refluxed at 110–120° C. for 5 hours. Solvent evaporation yielded a crystalline sample. Recrystallization from hexane-benzene (2:1) at 0° C. afforded an analytically pure sample of methoxyacetophenone (diethoxyphosphinyl) hydrazone. This intermediate is then reacted with the para-bromoacetophenone to produce the asymmetrical 4-methoxy-4'-bromoacetophenone azine as follows. A solution of the (diethoxyphosphinyl)hydrazone (3.72 mmol) in dried benzene (12 $cm^3$) was added dropwise to a solution of NaH (4.84 mmol) in dried benzene (10 $cm^3$) with stirring under nitrogen. When the hydrazone had reacted completely (formation of $H_2$ ceased), a solution of the appropriate para-substituted acetophenone (3.72 mmol) in dried benzene (8–12 $cm^3$) was added dropwise at 25° C. The liquid was decanted and washed with cold water until pH 7 was achieved. The solution was dried with $MgSO_4$. The solvent was evaporated off, yielding a crystalline sample. Recrystallization from hexane-benzene (2:1) at 0° C. afforded an analytically pure sample of the asymmetrical azine shown by the following structural formula. As will be understood by those skilled in the art, similar reaction routes can be followed to produce other asymmetrical azines embodying the present invention.

The synthesis procedure described generally above was used to prepare three asymmetrical acetophenone azines. These compounds identified herein as compounds 1, 2 and 3, respectively, were 4-methoxy-4'-bromoacetophenone azine, 4-methoxy-4'-cyanoacetophenone azine and 4-methoxy-4'-nitroacetophenone azine. The crystal structures for these three compounds were determined employing an Enraf-Nonius CAD4 diffractometer with Mo—$K_\alpha$ radiation ($\lambda$=0.709 30 Å) for compounds 1 and 2 and with Cu—$K_\alpha$ radiation ($\lambda$=1.540 56 Å) for compound 3. The crystal data and experimental parameters of these compounds are summarized in Table I. Absolute configurations of compounds 1 and 3 were determined by refinement of the n parameter. Selected bond lengths, angles and torsion angles for these compounds are set forth in Table II.

Figure 1:
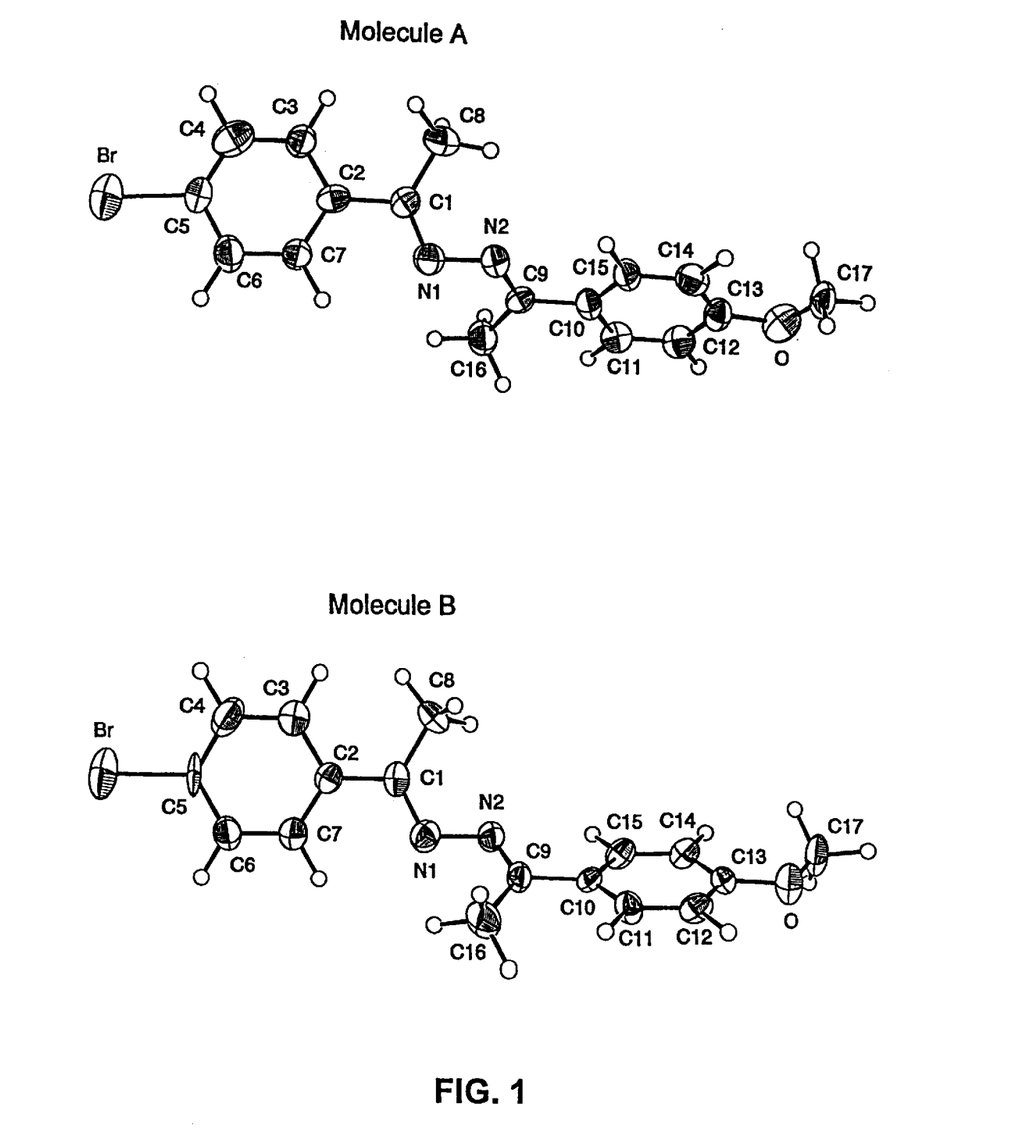
FIG. 1 is a perspective three dimensional illustration of showing two molecular forms of 4-methoxy-4'-bromoacetophenone azine.
Figure 2:
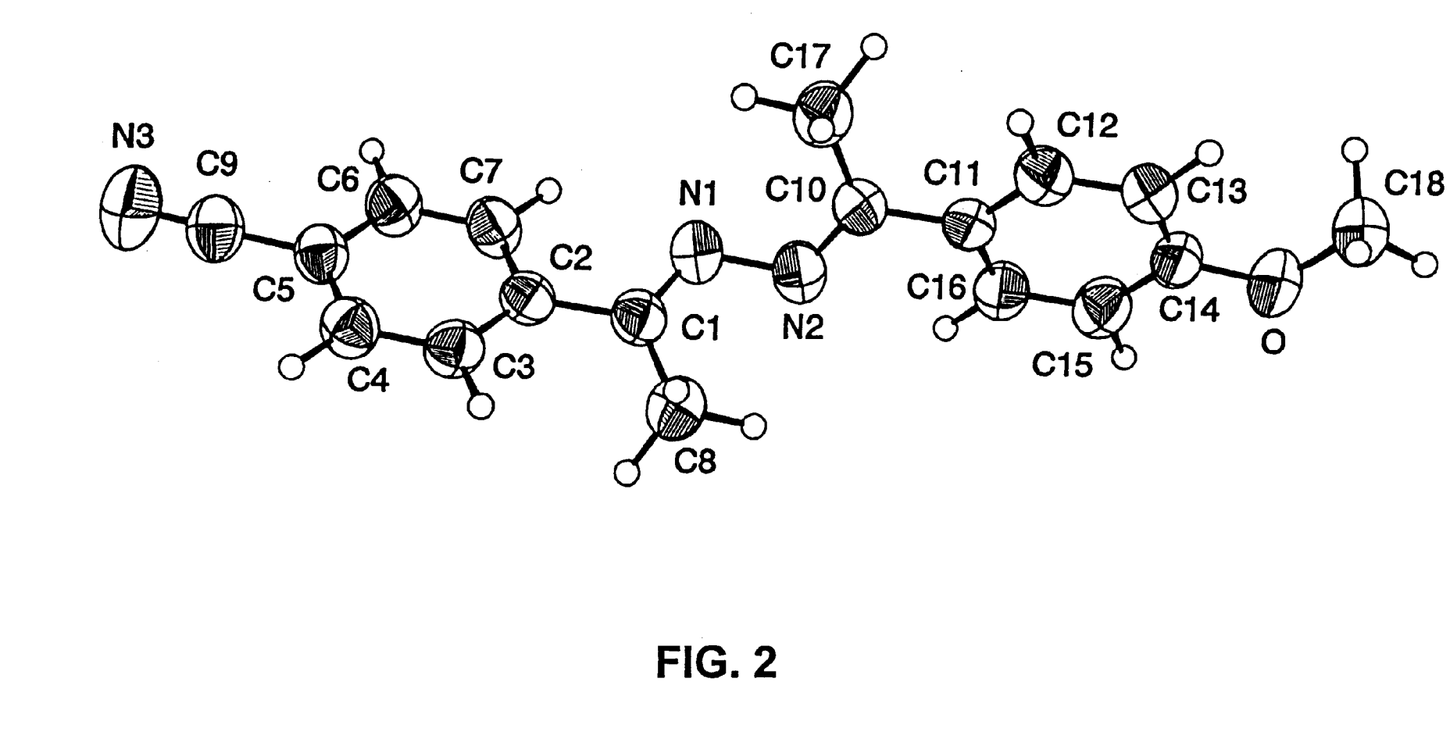
FIG. 2 is a perspective three dimensional illustration of a molecule of 4-methoxy-4'-cyanoacetophenone azine.
Figure 3:
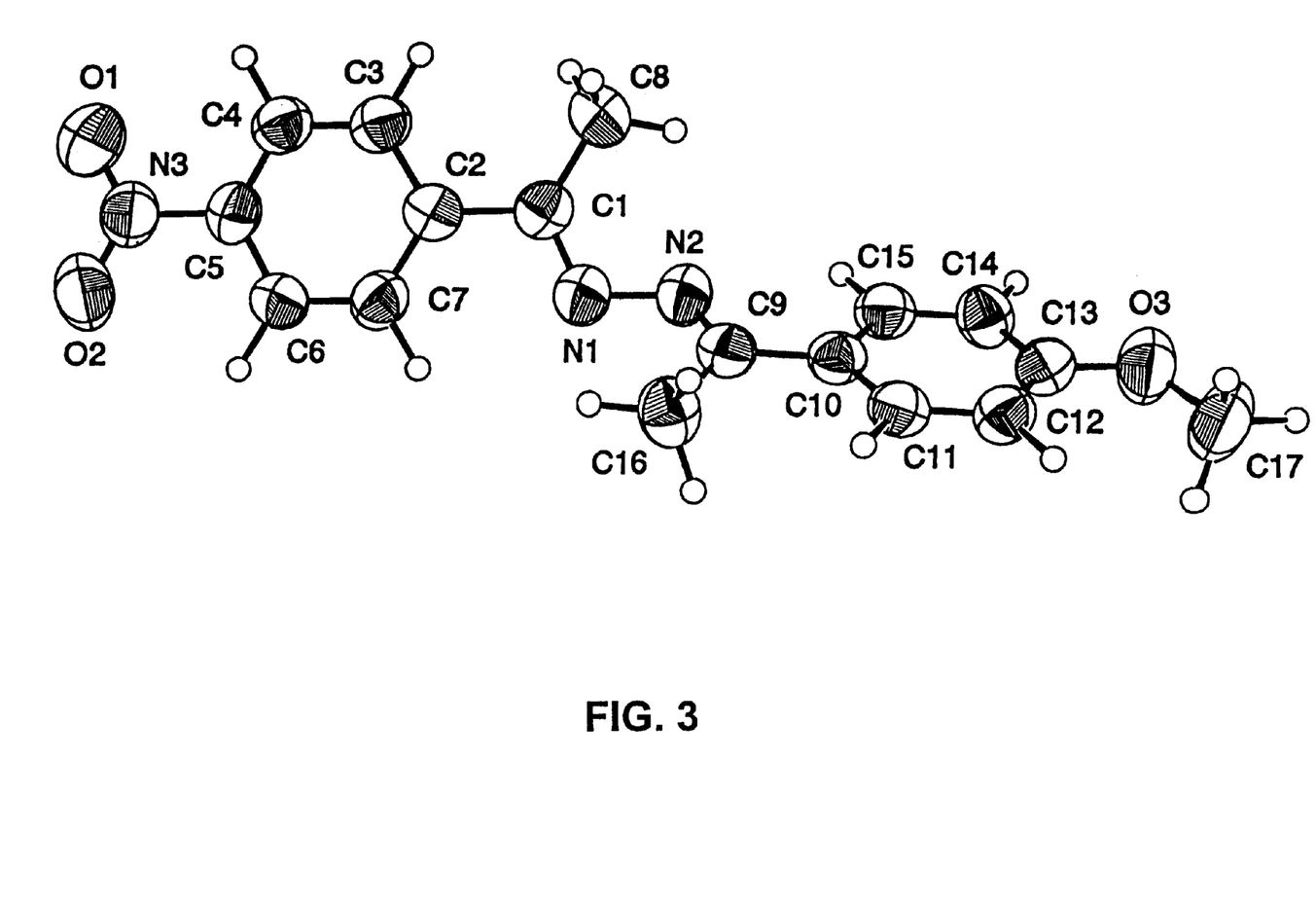
FIG. 3 is a perspective three dimensional illustration of a molecule of 4-methoxy-4'-nitroacetophenone azine.

Turning now to the drawings and referring initially to the FIGS. 1–3, there are illustrated perspective view of molecules for the compounds identified above as compounds 1, 2 and 3. FIGS. 1–3 are so-called perspective ORTEPII drawings of the type described in, Johnson, C. K., ORTEPII, ORNL-5138, Oak Ridge National Laboratory, Tennessee (1976). The 4-methoxy-4'-bromoacetophenone azine exists in the crystalline structure in two symmetrically independent molecular forms which are designated in FIG. 1 as molecule A and molecule B. The numbering schemes used in the following tables are indicated in FIG. 1 and also in FIGS. 2 and 3 which are perspective ORTEPII drawings of 4-methoxy-4'-cyanoacetophenone azine and 4-methoxy-4'-nitroacetophenone azine, respectively.

Figure 4:
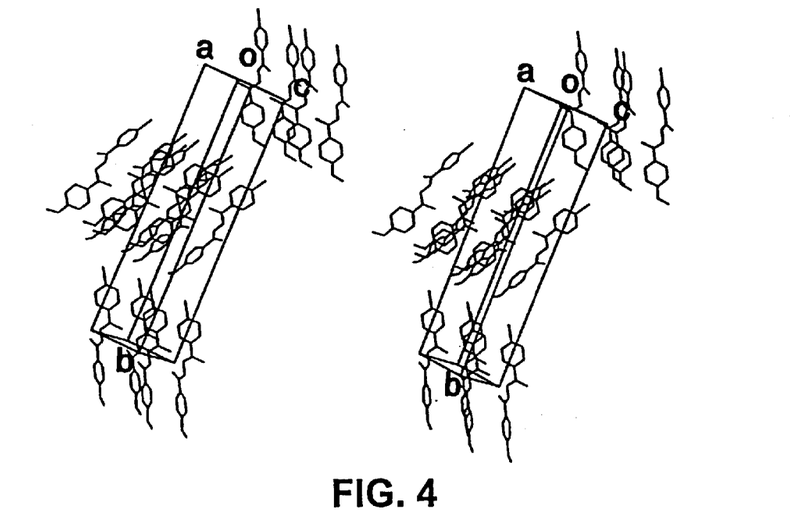
FIG. 4 is a schematic illustration of a packing diagram for 4-methoxy-4'-bromoacetophenone azine.
Figure 5:
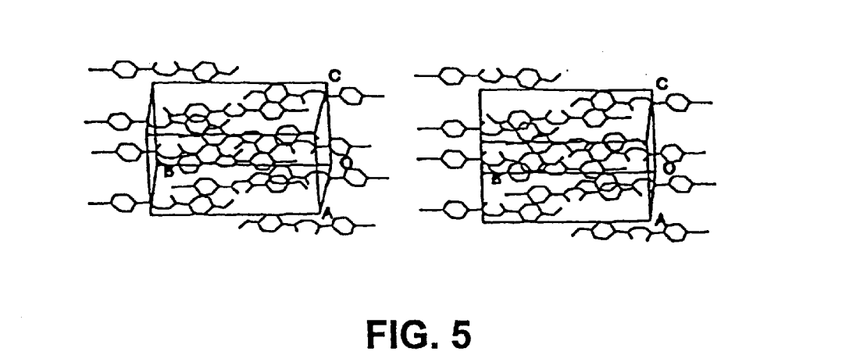
FIG. 5 is a schematic illustration of a packing diagram for 4-methoxy-4'-cyanoacetophenone azine.
Figure 6:
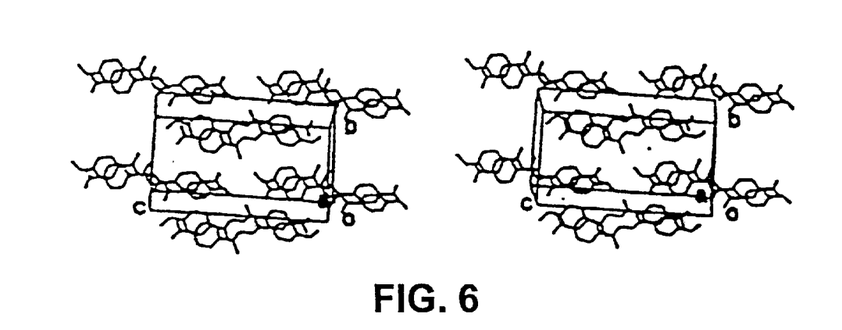
FIG. 6 is a schematic illustration of a packing diagram for 4-methoxy-4'-nitroacetophenone azine.

FIGS. 4, 5 and 6 present the schematic illustrations of packing diagrams for the crystalline forms of, 4-methoxy-4'-bromoacetophenone azine, 4-methoxy-4'-cyanoacetophenone azine, and for 4-Methoxy-4'-nitroacetophenone azine, respectively. Each packing diagram illustrates a unit cell for the crystalline material of the particular azine represented. These packing diagrams may be considered in relation to the packing diagrams shown in FIG. 2 of the aforementioned Glaser et al paper.

Figure 7:
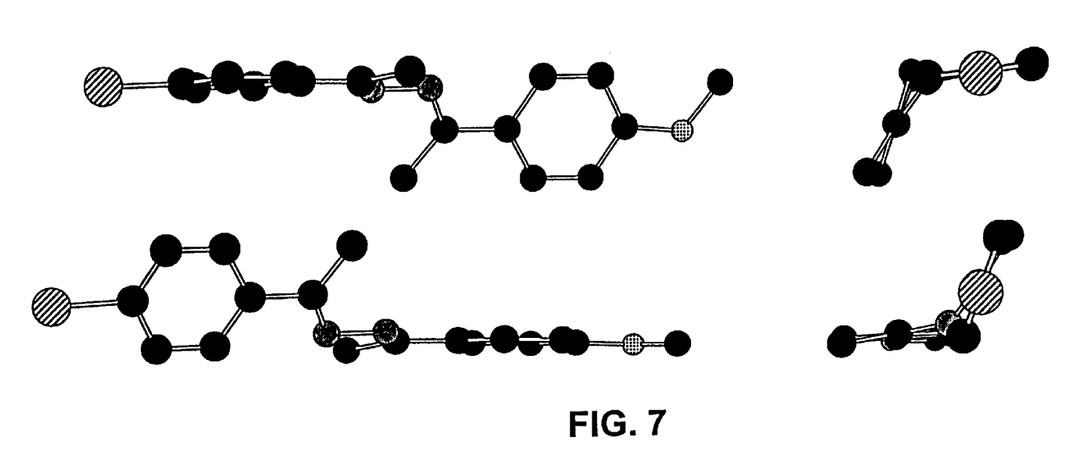
FIG. 7 is a perspective three dimensional illustration of adjacent molecules of 4-methoxy-4'-bromoacetophenone azine in a parallel packing configuration.

FIG. 7 illustrates a parallel packing alignment of the symmetry independent molecular forms 4-methoxy-4'-bromoacetophenone azine which are designated as molecules A and B in FIG. 1. Two views of each molecule are shown. The views on the left-hand side of the figure generally indicating the molecules as they exist along an axis of symmetry corresponding to the acceptor and donor groups and the drawings to the right-hand of FIG. 7 illustrate the molecules as generally shown along a transverse axis from the bromine side of the molecules. Also, it will be recognized that in FIG. 7 the hydrogen atoms are not shown.

Figure 8:
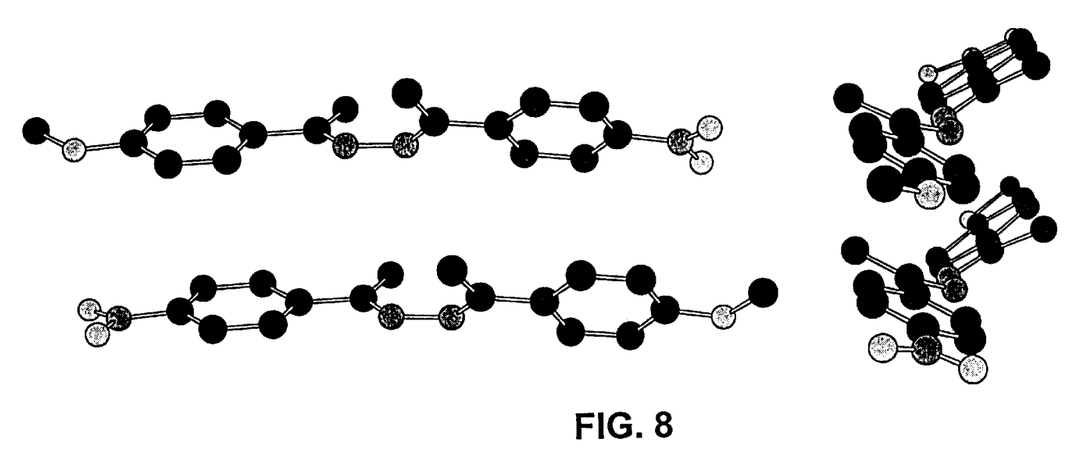
FIG. 8 is a perspective three dimensional illustration of adjacent molecules of 4-methoxy-4'-nitroacetophenone azine in an antiparallel packing configuration.

FIG. 8 illustrates an anti-parallel packing alignment for two molecules of 4-methoxy-4'-nitroacetophenone azine. As discussed hereinafter, 4-methoxy-4'-nitroacetophenone azine assumes a highly parallel alignment in solution under an applied electric field. However, this molecule crystallizes into an anti-parallel packing alignment in which the methoxy group (shown to the left in the upper molecule) is adjacent to the nitro group (shown to the left in the bottom molecule) of FIG. 8.

TABLE I

|  | 1 | 2 | 3 |
|---|---|---|---|
| Chemical formula | $C_{17}H_{17}BrN_2O$ | $C_{18}H_{17}N_3O$ | $C_{17}H_{17}N_3O_3$ |
| Molecular weight | 345.23 | 291.35 | 311.34 |
| Crystal system | Monoclinic | Monoclinic | Orthorhombic |
| Space group | P 21 | P 21/c | P 212121 |
| a/Å | 7.766(3) | 10.002(3) | 7.8946(8) |
| b/Å | 31.949(3) | 19.461(3) | 10.5559(8) |
| c/Å | 6.339(20) | 9.0010(20) | 19.1061(9) |
| β/deg | 95.380(20) | 115.764(9) |  |
| θ range (cell) | $20 \leq 2\theta/\text{deg} \leq 30$ | $20 \leq 2\theta/\text{deg} \leq 30$ | $40 \leq 2\theta/\text{deg} \leq 50$ |
| V/Å³ | 1565.9(10) | 1577.9(6) | 1592.20(21) |
| Z | 4 | 4 | 4 |
| $D_X$/g cm⁻³ | 1.464 | 1.226 | 1.299 |
| Radiation (λ/A) | Mo-Ka (0.709 30) | Mo-Ka (0.709 30) | Cu-Ka (1.540 56) |
| μ/cm⁻¹ | 26.0 | 0.7 | 7.1 |
| T/K | 293 | 293 | 293 |
| θ range (data) | $2 \leq 2\theta/\text{deg} \leq 46$ | $2 \leq 2\theta/\text{deg} \leq 46$ | $2 \leq 2\theta/\text{deg} \leq 120$ |
| Reflections measured | 3800 | 2305 | 1833 |
| Independent reflections | 3456 | 2167 | 1805 |
| Observed reflections | 2510, I > 1.5δ(I) | 1686, I > 2.0δ(I) | 1420, I > 1.8δ(I) |
| h | −9→9 | −10→9 | 0→9 |
| k | 0→40 | 0→21 | 0→13 |
| l | 0→8 | 0→9 | 0→23 |
| R; $R_w$; S | 0.061; 0.061; 1.48 | 0.047; 0.065; 1.95 | 0.052; 0.060; 1.74 |
| F(000) | 703.05 | 616.22 | 658.07 |
| Maximum Δ/δ | 4.8% | 0.4% | 0.2% |
| Δρ: max.; min./e Å⁻³ | 0.480; −0.400 | 0.150; −0.200 | 0.150; −0.250 |

TABLE II

Selected bond lengths (Å), angles (*) and torsion angles (*)

|  | 1a | 1b | av(1)* | 2ª | 3ᵇ |
|---|---|---|---|---|---|
| X1-C5 | 1.916(9) | 1.894(8) | −11 | 1.438(4)ᶜ | 1.462(4) |
| X2-C13 | 1.402(12) | 1.374(11) | −14 | 1.367(3)ᵈ | 1.370(4) |
| N1–N2 | 1.396(11) | 1.375(11) | −11 | 1.390(3) | 1.396(4) |
| N1–C1 | 1.253(12) | 1.314(12) | 31 | 1.277(3) | 1.293(4) |
| N2-C9 | 1.295(11) | 1.282(12) | −7 | 1.278(3)* | 1.273(4) |

TABLE II-continued

Selected bond lengths (Å), angles (*) and torsion angles (*)

|  | 1a | 1b | av(1)* | 2[a] | 3[b] |
|---|---|---|---|---|---|
| C1–C2 | 1.500(13) | 1.445(12) | −28 | 1.485(3) | 1.495(4) |
| C9–C10 | 1.484(13) | 1.485(12) | 1 | 1.478(3)[f] | 1.476(4) |
| C2–C3 | 1.389(13) | 1.409(13) | 10 | 1.389(3) | 1.410(4) |
| C3–C4 | 1.393(15) | 1.368(15) | −13 | 1.379(3) | 1.372(5) |
| C4–C5 | 1.379(15) | 1.376(15) | −2 | 1.382(3) | 1.367(5) |
| C10–C11 | 1.406(12) | 1.387(12) | −9 | 1.382(3)* | 1.381(4) |
| C11–C12 | 1.377(14) | 1.357(13) | −10 | 1.390(3)[b] | 1.396(5) |
| C12–C13 | 1.379(13) | 1.377(12) | −1 | 1.370(4)[i] | 1.379(5) |
| N2–N1-C1 | 114.4(7) | 116.9(7) | 13 | 116.47(20) | 115.0(3) |
| N1–N2-C9 | 116.1(7) | 115.0(7) | −6 | 116.84(2)[j] | 115.6(3) |
| N1-C1–C2 | 115.7(8) | 117.5(8) | −9 | 115.98(21) | 114.2(3) |
| N1-C1–C8 | 125.3(9) | 121.8(8) | −8 | 123.92(21) | 124.5(3) |
| C2–C1–C8 | 118.9(8) | 120.7(8) | 9 | 120.08(21) | 121.3(3) |
| C1–C2–C3 | 121.2(8) | 120.6(8) | −3 | 121.58(21) | 120.2(3) |
| N2-C9–C10 | 117.0(8) | 116.4(7) | −3 | 116.92(21)[k] | 116.9(3) |
| N2-C9–C16 | 122.9(8) | 123.8(8) | 4 | 123.41(21)[l] | 123.6(3) |
| C10–C9–C16 | 120.1(8) | 119.7(8) | −2 | 119.67(21) | 119.5(3) |
| C9–C10–C11 | 120.3(7) | 122.1(7) | 9 | 121.95(21) | 122.8(3) |
| C1-N1–N2-C9 | −137.5(10) | 136.1(10) | −7 | −117.9(2)[m] | 134.1(4) |
| N2–N1-C1–C8 | 4.1(5) | −0.6(5) | −24 | 5.1(1) | −4.5(2) |
| N1–N2-C9–C16 | 2.7(5) | −4.9(5) | −38 | 5.2(1)[a] | −3.0(2) |
| N1-C1–C2–C7 | 13.5(5) | −3.1(5) | −83 | 14.0(1) | −1.4(2) |
| N1-C1–C2–C3 | −163.8(11) | 175.5(11) | −58 | −164.8(3) | −179.6(4) |
| N2-C9–C10–C15 | 8.9(5) | −17.9(5) | −134 | 16.3(1)* | −5.2(2) |
| N2-C9–C10–C11 | −172.(11) | 160.9(10) | 56 | −162.7(3)[p] | 172.9(4) |

[a]X1 = C9, X2 = O, [b]X1 = N3, X2 = O3, *X1 = C9 *X2-C14, *N2-C10, [f]C10–C11, *C11–C12, [h]C12–C13, [i]C13–C14, [j]N1–N2-C10, [k]N2-C10–C11, N11-C10–C17, [m]C1-N1–N2-C10, *N1–N2-C10–C17, *N2-C10–C11–C16, [p]N2-C10–C11–C12.

Referring back to aforementioned Glaser et al paper, resonance forms for certain symmetrical azines are discussed and reported in this paper in connection with crystal and electronic structures presented in various resonance forms shown therein under the denomination Schemes 1 and 2 and X-ray data and crystallinity data together with selected bond lengths and angles and comparative structural data are shown in Glaser et al in Tables 2, 3 and 4. Corresponding three dimensional molecular configurations and corresponding packing diagrams for certain of the azines described there are shown in FIGS. 1 and 2 of the Glaser et al paper. For further description of these parameters for symmetrical azines, reference may be had to the aforementioned Glaser et al paper, the entire disclosure which is incorporated herein by reference.

Table III presents comparative structural parameters derived from the X-ray data presented in Glaser et al for symmetrical azines and corresponding data for asymmetrical azines embodying the present invention. In Table III, certain selected bond lengths are shown along with torsion angles, τ, as well the phenyl twist angles, $\phi_A$ and $\phi_B$ for the donor substituted and acceptor substituted phenyl groups.

TABLE III

Comparison of X-ray structural parameters of symmetrical and asymmetrical acetophenone azines

| | Asymmetrical* | | | | | Symmetrical | | | |
|---|---|---|---|---|---|---|---|---|---|
| | 1a MeO-Br | 1b MeO-Br | av(1) MeO-Br | 2 MeO-CN | 3 MeO-NO$_2$ | 4 MeO | 5 Br | 6 CN | 7 NO$_2$ |
| X-C | 1.916 | 1.894 | 1.905 | 1.438 | 1.462 | 1.364 | 1.904 | 1.435 | 1.456 |
| Y-C | 1.402 | 1.374 | 1.388 | 1.367 | 1.370 | | 1.891 | | 1.467 |
| N-N | 1.396 | 1.375 | 1.386 | 1.390 | 1.396 | 1.409 | 1.383 | 1.397 | 1.398 |
| N=C$_A$ | 1.253 | 1.314 | 1.284 | 1.277 | 1.293 | 1.281 | 1.264 | 1.277 | 1.280 |
| N=C$_B$ | 1.295 | 1.282 | 1.289 | 1.278 | 1.273 | | 1.269 | | 1.273 |
| C$_{ipoo}$-C$_A$ | 1.500 | 1.445 | 1.473 | 1.485 | 1.495 | 1.479 | 1.478 | 1.475 | 1.491 |
| C$_{ipoo}$-C$_B$ | 1.484 | 1.485 | 1.485 | 1.478 | 1.476 | | 1.477 | | 1.482 |
| τ | 137.5 | 136.1 | 136.8 | 117.9 | 134.1 | 180.0 | 124.6 | 180.0 | 152.0 |
| $\phi_A$ | 13.5 | 3.1 | 8.3 | 14.0 | 1.4 | 10.7 | 27.2 | 0.5 | 1.2 |
| $\phi_B$ | 8.9 | 17.9 | 13.4 | 16.3 | 5.2 | | 20.9 | | 14.0 |

*Y = MeO. A and B refer to the fragments with X and Y, respectively.

The effects of asymmetric substitution on related azines are discussed below with respect to Tables IV and V which graphically present structural resonance forms identified as forms B, C and D. In Table III, configuration A represents the principal resonance form for azines, the forms B reflect the polarity of the C=N bond (B1) and possible delocalizations of positive charge onto the ortho (o-B2 and o'-B2) and para positions (B3), and the forms C are derived from B1 by shifting n-electrons in such a fashion that negative charge is delocalized from the N-atom onto the azine C-atom (C1), the ortho position (o-C2 and o'-C2), and the para position (C3). The C-forms disperse negative charge from a nitrogen atom onto carbon atoms, while a positive charge is placed on $sp^2$-hybridized carbon atoms in all of the B-forms. One might thus expect larger contributions from B- than from C-forms.

TABLE IV

TABLE V

All the resonance forms B and C are shown for one half of the molecule and the related counterparts B' and C' should also be considered. In symmetrical azines of the type disclosed in the aforementioned Chen and Glaser papers, these sets of resonance forms have pairwise equal weight. The asymmetrical azines of the present invention differ from the symmetrical azines fundamentally in that the (near-) degeneracy of the pairs B and B' (or C and C') is eliminated on purpose. Table IV shows only those B and C forms that place positive or negative charges, respectively, in the donor or acceptor substituted rings. Aside from B and C, other resonance forms need to be considered in which the types of shift leading to B and C both occur, and this is exemplified by the D forms, shown in Table V of the 4-methoxy-4'-nitro system. These D forms also reflect the potential for the formation of the so-called quinoid resonance forms.

NLO materials require large macroscopic dipoles and hyperpolarizabilities β and, to obtain high values, it is appropriate to increase the lengths of the π-system and vary the strengths of the donor and acceptor groups. In the two state approximation, one is guided by the rule that the ground and excited states should differ greatly in their dipole moments, that is, the ground and excited states should differ in the relative contributions of the 'nonpolar resonance form' A and the 'polar resonance form' D.

The resonance forms can be related to the geometries as outlined in the discussion of symmetrical azines in the aforementioned Glaser paper. On the donor side, significant contributions from B will result in longer C=N bonds, shorter $C_{Ipso}-C_{azine}$ bonds (B1–B3,D), and shorter D—C bonds (B3, D). On the acceptor side, significant contributions from C will result in shorter N—N bonds, longer C=N bonds, shorter $C_{Ipso}-C_{azine}$ bonds (C1–C3), and shorter C—A bonds (D). Most of these structural changes indicate whether charge dispersal (of either type) occurs, but they do not indicate whether the dispersed charge is positive or negative. The N—N bond length is an exception, it should shorten only if significant negative charge dispersal occurs. Such negative charge dispersal onto the phenyl rings would be favoured in N—N trans conformations. In contrast, significant contributions by the B forms would lead to electron density accumulations of the azine-N atoms which might eventually lead to an N—N gauche preference because of electron-electron repulsion. In that event, the extended π-system becomes interrupted and the consideration of azines as dimines becomes appropriate. Finally, any significant conjugative interaction of the X substituent should favor coplanarity of the phenyl ring with the —RC=N— group.

In studies of conjugation-based structural data, the selection of the proper reference is important and comparative analyses are required for series of closely related molecules that allow for the study of the changes of structural parameters. The symmetrical azines can be used to provide reference parameters. Comparisons of selected bond lengths and torsion angels of asymmetrical compounds, substituted with, MeO—Br, MeO—CN and Me—NO₃ with the symmetrical para-disubstituted acetophenone azines disubstituted with MeO, Br, CN and NO₂ groups, respectively, are reported in Table III. Even with the existence of this best possible reference data, the unambiguous identification of intrinsic features remains complicated by packing effects, and one needs to keep in mind, and evaluate whenever possible, the sensitivity of the structural parameters to crystal packing.

As noted previously, the alignment of the asymmetric molecular systems of the present invention provide substantial macroscopic dipole moments. More specifically, the nonlinear optical materials of the present invention can be characterized as azine bridged di-arenes exhibiting a substantial hyperpolarizability by employing polar donor and acceptor groups with arene type alignment units incorporating spacer units that tend to minimize the dipole moment of a chromophore in the ground state while allowing for large dipole moments when the chromophore is in excited state upon interaction with applied laser light. The compositions of the present invention can be characterized as azine-bridged di-arenes having a substantial net macroscopic dipole moment and characterized by the formula:

$$D-Ar_1-B-Ar_2-A \qquad (1)$$

In formula (1), $Ar_1$ and $Ar_2$ are arenyl groups which may be the same or different. D is an electron donor on the arenyl group $Ar_1$, A is an electron acceptor substituent on the second arenyl group $Ar_2$, and B is an azine bridge interconnecting the first and second arenyl groups. The crystalline di-arene 4-methoxy-4'-bromoacetophenone azine of formula 1 has a dipole alignment factor A of about 0.7%. That is, the macroscopic dipole for the crystal $\mu_{cryst}$ is at least 70% of the sum of the macroscopic molecular dipoles as indicated by the relationship:

$$\mu_{cryst} \geq 0.7 \Sigma \mu_{mol}$$

In this equation, $\mu_{cryst}$ is the macroscopic crystalline dipole and $\mu_{mol}$ is the molecular dipole. Preferably, the alignment factor of the NLO material of the present invention is at least 0.5. That is, $\mu_{cryst} \geq 0.5 \Sigma \mu_{mol}$.

The arenyl groups normally will take the form of mononuclear aromatics including heterosubstituted aromatics. Thus, each Ar group normally will be a benzene ring, but it can be a corresponding heterocompound such a pyridine or pyrimidine or another heterocompound. The benzyl or other mononuclear aromatic may be substituted other than the substitution provided by the donor or acceptor moiety. For example, substituted aromatics such as toluene, aniline or even cumene may be employed depending upon the nature and bulk of the electron acceptor and electron donor substituents. In addition, the arene groups may take the form of polynuclear condensed aromatics such as naphthalene and anthracene. Heterosubstituted derivatives of such polynuclear aromatics such as quinoline may also be employed.

The donor substituent D may be any suitable functional group or modified, i.e. derivatized or complexed, functional group, that functions in the asymmetric chromophore in a manner to be electron donating. The substituent A can be any suitable functional group or modified, (derivatized, complexed) functional group that functions in the chromophore to be electron withdrawing. The remainder of the asymmetrical chromophore can be characterized as a "connector" interposed between the donor and acceptor groups. For the purposes of discussion, the connector can be further partitioned into "alignment units" (AU) and "spacer units" (SU). The alignment unit may be characterized as any part of the connector that is involved in intermolecular bonding. Thus, the alignment unit will include the aromatic portion of the chromophore which is substituted with the donor and acceptor groups. The "spacer" unit can be characterized as any other part of the "connector" and includes the azine bridge which functions together with the arenyl groups to promote parallel packing of the dipolar molecules.

As described in greater detail below, the alignment unit and the "spacer unit" will take the form of conjugated π systems although they are not necessarily in conjugation nor are they invariably conjugated. The number of "alignment units" and "spacer units" in the chromophore system may vary although there must necessarily be at least one alignment unit. The preferred dialkylene azinyl groups employed as bridges in the present invention can be characterized in terms of functional units as follows:

donor-$AU_d$-SU-$AU_a$-acceptor

In applying this nomenclature to an asymmetrical acetophenone azine such as compounds 1, 2 and 3 referred to above, the methoxy group functions as the donor, the first phenyl group corresponds to the alignment unit $AU_d$, the azine bridge is the spacer unit, SU, the second phenyl group corresponds to $AU_a$ and the bromo, cyano or nitro groups correspond to the acceptor group.

In a more general sense, the donor and/or the acceptor need not be directly substituted on an alignment unit, but can in turn be connected to the alignment unit by means of a spacer unit. Similarly, the spacer unit need not be symmetrical about the nitrogen-nitrogen bond. The azine spacer unit may in turn be interconnected to the alignment units by further spacers at one or both sides of the chromophore. This generic system can be described generally by the nomenclature:

donor-spacer-$AU_d$-spacer-$AU_a$-spacer-acceptor

The spacer units of the chromophores embodying the present invention function to reduce the dipole moment in the ground state (where it is not excited by light waves or other electromagnetic radiation) while permitting a large dipole moment when the chromophore is excited by applied electromagnetic radiation. This condition is satisfied by minimal ground state dipole moments due to the azine bridges employed in the present invention. This condition affords the desired parallel alignment since it causes intermolecular attractions that compensate for the intermolecular electrostatic repulsion terms. Preferably, the spacer unit is selected to provide a configuration which can be considered to be a combination of two fragments, both of which function as electron accepting groups. This construction results in a built-in configuration for the molecules that provides a sequence:

donor-(SU-acceptor-1)-(SU-acceptor-2)-acceptor and causes partial cancellation of the dipole moment in the ground state. Alternatively, the spacer unit can be provided in a configuration that results in a combination of two fragments that both serve as electron donating groups. This configuration results in the sequence:

donor-(SU donor-1)-(SU-donor-2)-acceptor and again results in partial cancellation of the dipole moment in the ground state.

As described previously, the preferred configurations employ mononuclear aromatics such as para substituted benzyl groups as alignment groups, but the donor and/or acceptors may be in the ortho or para positions. Also, there may be several donors in the para and ortho positions on an alignment unit and there likewise may be several acceptors in the para and ortho positions of the alignment unit at the opposite end of the chromophore.

While as discussed previously, the azine functional groups typically have racemically configured methyl groups attached thereto, the chromophores of the present invention are not limited to this arrangement. As outlined below, rather than methyl groups, one or both substituents may be another alkyl group, an alkenyl group, an alkynyl group or another aromatic group. Alternatively, one or both of the substituents need not be present. That is, rather than a substituent group, hydrogen may be present at one or both locations. While the normal configuration includes an aromatic system at the donor and acceptor ends of the molecule attached directly to the azine functional group, the chromophore can include additional spacers between the azine group and the aromatic system. By way of example, configurations of this nature can include —CR=CR— units between the functional group and the aromatic system on one or both sides of the azine functional group with the numbers of such units being the same or different for the two sides of the azine group. An example of such a system is shown by the following structural configuration:

In the aforementioned structure as well as the structures which follow, X indicates one of the acceptor and donor groups and Y indicates the other of the acceptor and donor groups. Thus, X may be the acceptor group and Y the donor or X may be the donor and Y the acceptor. R indicates hydrogen atoms or alkyl groups which are generally the same. $R_2$ and $R_3$ can be alkyl groups or hydrogen groups and can be the same or different. The two-atom spacer units in the foregoing structure could contain heteroatom analogs. For example, CR could be replaced by nitrogen or phosphorus. For example, some of the units which would normally be CR=CR could be CR=N or N=CH. Another possible configuration could have constraints similar to those described above but with a spacer unit containing a alkyne group.

Another suitable configuration of chromophores embodying the present invention includes an aromatic group which functions as a spacer between the azine functional group and the arenyl alignment groups. An example of such chromophore which also employs a naphthalene group as one of the alignment units is shown below:

The compounds described thus far have structures that the electron donor and electron acceptor groups are substituted directly on an aromatic ring. In yet another embodiment of the invention, one or both of the alignment units can be provided with a spacer between the alignment unit and the donor and acceptors or between only one alignment unit and a donor or acceptor. An example of a chromophore embodying one spacer between an alignment unit and a donor or acceptor is illustrated below.

Preferred chromophores embodying the present invention employ azine functional groups and show significant cancellation of the dipole moment in the ground state. Preferred azine groups include the dimethyl substituted azines as exemplified by the compounds identified previously as compounds 1, 2 and 3. The structural formula for compound 1 (4'-Bromo-substituted-4-acetophenone azine) is shown below:

The methoxy-cyano and methoxy-nitro chromophores show similar configurations to those shown above for the methoxy-bromo chromophore. For the 4-methoxy-4'-bromoacetophenone azine, near perfect dipole parallel alignment was realized in the solid state. The macroscopic dipole was found to be about $0.7\Sigma\mu_{mol}$ and the chromophore density was 100%. The methoxy-cyano and the methoxy-nitro compounds showed good NLO effects in solution. Another compound exhibiting good NLO effect in solution was 1-p-cyano-phenyl-p-dimethylaminophenyl 2,3, diazapentadiene having only a single methyl substituent in the spacer group. This compound and also a similar compound, 4-p-nitrophenyl-1-p-diaminophenyl-2,3, diazapentadiene showed good NLO effects in solution. The structural formulas for these respective compounds are shown below:

The materials described above, all incorporated azine functional groups characterized by the group —C=N—N=C—. Other suitable spacer groups which cause partial cancellation of the dipole moment in the ground state are by way of example, vinylimine characterized by the group —C=N—C=C— may also be employed. A chromophore of this general configuration can be characterized by the following general formula:

D—Ar$_1$—E$_1$—C=N—C=C—E$_2$—Ar$_2$—A

Other chromophores which may be employed in carrying out the present invention, include the following compounds in which the methoxy group is employed as the electron donor:

4'-fluoro-4-methoxyacetophenone azine

4'-chloro-4-methoxyacetophenone azine

4'-ethoxycarbonyl 4-methoxyacetophenone azine

Various piperidines may be employed such as 4'-nitro 4-piperidinoacetophenone azine.

Various compounds in which amino groups are used as the electron donor include:

4'-chloro 4-aminoacetophenone azine

4'-bromo 4-aminoacetophenone azine

4'cyano 4-aminoacetophenone azine

4'-nitro 4-aminoacetophenone azine

From the foregoing description, it will be recognized that the alignment units of the chromophores embodying the present invention may take the form of any suitable group which will provide an intermolecular interaction between the adjacent chromophore molecule in the molecular structure. As a practical matter, the alignment units may be characterized as having conjugated π systems wherein, while they will normally be mononuclear groups may be conjugated dinuclear groups. The spacer, preferably an azine performs two important functions. First, of course, the spacer unit functions to link the acceptor half and the donor half of the molecule together. The second important function provided by the azine, or other π conjugated group, is in minimizing the dipole moment of the molecule in the ground state, i.e. in the state in which it is not subject to applied electromagnetic energy in or near the visible light spectrum. By providing the requisite low dipole moment in the ground state, the chromophore molecules can be forced into the desired alignment which results in the substantial macroscopic dipole of the crystal.

The donor and acceptor groups may be any suitable functional groups which can be substituted on the aryl groups, normally on the para position with respect to the bridge, and which function in the chromophores to perform the electron donating and electron withdrawing activities. The donor and acceptor substituents normally will have transverse dimensions when substituted on the aryls group which are less than corresponding diameter of the aryl group. Somewhat bulky donor and acceptor groups may be employed, although as will be recognized from the foregoing description they should not be sufficiently bulky to hinder the packing of the molecules through the functioning of the alignment groups. Suitable electron acceptor groups include bromo, fluoro, cyano and nitro groups as described above as well as acyls, carboxy and carbonyl groups and various other substituent groups which can be generally characterized as electron acceptors. Suitable electron donors include ethers, such as the methoxy groups described above, thioethers, amines, alkylamines, piperidines and various other functional groups which can be broadly characterized as electron donors. While electron donor and electron acceptor groups as delineated above will usually be preferred, it is to be recognized that numerous electron donors and electron acceptors are available and will be recognized by those skilled in the art. For a comprehensive description of such electron donors and electron acceptors, reference is made to *A Survey of Hammett Substituent Constants and Resonance and Field Parameters*, Amer. Chem. Soc., *Chem. Rev.*, Vol. 91, pp. 165–195 (1991), the entire description of which is incorporated herein by reference.

As a practical matter, it usually will be preferred to provide arenyl groups which are mononuclear aryl groups such as benzyl groups. The preferred bridge structure is a conjugated azinyl group which can be characterized by the structure:

(3)

R' and R" are hydrocarbon groups in a racemic configuration as indicated by the stereochemical relationship of the R' and R" groups. As described in the preferred embodiments below, R' and R" may each be methyl groups.

As will be recognized from the foregoing description, the nonlinear optical materials of the present invention will find application in various processes implementing laser radiation. A particular application, of course, is in the frequency modification of laser energy, as in the second harmonic generation of an input optical wave that undergoes frequency doubling. Thus, a laser source of coherent light at a designated fundamental frequency may be applied to a cell of crystalline 4-methoxy-4'-bromoacetophenone azine to produce a frequency doubled beam at a second harmonic frequency which can then be applied to a suitable utilization system. By way of example, such an utilization system may comprise an averaging and measuring system as disclosed in U.S. Pat. No. 5,163,060 to Mitre. Similar applications can be carried out in accordance with the present invention in order to produce light beams of other modified electromagnetic characteristics. Thus, the NLO materials of the present invention may be employed in amplitude modulation of a laser beam or to produce phase changes in a laser with the output beams being applied to suitable utilization systems, as will be understood by those skilled in the art. Such utilization systems include modulation systems and photonic devices of the type discussed in Wang et al, *Traveling wave electro-optic phase modulator using cross-linked nonlinear optical polymer, Appl. Phys. Lett.*, American Institute of Physics, Vol. 65 (8), pp. 929–931 (August 1994), the entire disclosure of which is incorporated herein by reference.

Another application of the present invention employs the use NLO chromophores of the present invention in so-called thin films. Those films normally will be of a thickness of less than one micron, usually substantially less. Such thin films can be used in photonic applications such as display fabrication. Typically, in a thin film application, a layer of the NLO chromophore embodying the present invention can be placed on or adhered to a substrate surface which can be metal, ceramic or polymeric. If desired, the various NLO chromophores embodying the present invention can be modified by the substitution of side chains on either the alignment units or the spacer units or both which function in essence to "connect" the chromophore to the substrate material. The thin film NLO materials of this embodiment of the invention can be of any suitable thickness, generally ranging from a thickness of a one molecule thick layer, about 10 Å, up to perhaps 1,000 Å in thickness. The NLO thin film may be used in laminate applications. For example, the NLO thin film may be adhered to the substrate material and in turn, a layer of transparent material placed overlaying the NLO thin film to provide a protective layer. Several layers of NLO thin film may similarly be employed. For example, a first layer of NLO film may be adhered to the substrate material, this material can be covered by a second layer of intervening material and this in turn followed by a second NLO film.

Having described specific embodiments of the present invention, it will be understood that modifications thereof may be suggested to those skilled in the art, and it is intended to cover all such modifications as fall within the scope of the appended claims.

What is claimed:

1. A nonlinear optical material comprising a recrystallized crystalline azine bridged di-arene having a net macroscopic dipole moment and described by the formula:

$$D—Ar^1—B—A^2—A$$

wherein:
Ar$^1$ is a first arenyl group and AR$^2$ is a second arenyl group which may be the same as or different from Ar$^1$;
D is an electron donor substituent on said first arenyl group;
A is an electron acceptor group on said second arenyl group; and
B is an azine bridge interconnecting said first and second arenyl groups and is a conjugated azinyl groups; and is a conjugated azinyl group characterized by the formula:

$$—E^1=N—N=E^2—$$

wherein E$^1$ and E$^2$ are each independently C$^1$–C$^4$ linear groups which may be the same or different and which are substituted with substituent side groups R' and R" respectively, wherein R' and R" are racemic and each independently contain one or two carbon atoms, said material having a macroscopic dipole alignment factor of at least 0.1.

2. The composition of claim 1, wherein said material has a macroscopic dipole alignment factor of at least 0.5.

3. The composition of claim 1, wherein E$_1$ and E$_2$ are each independently methylene or ethylene which can have substituent side groups which contain 1 or 2 carbon atoms.

4. The composition of claim 3, wherein Ar$_1$ and Ar$_2$ are each phenyl groups.

5. The composition of claim 4, wherein D and A are each in the para position with respect to said bridge.

6. The composition of claim 5, wherein R' and R" are methyl groups.

7. The composition of claim 6, wherein E$_1$ and E$_2$ are each methylene groups.

8. The composition of claim 1, wherein D is an electron donor selected from the group consisting of ethers, thioethers, amines, alkylamines, dialkylamines and piperidines.

9. The composition of claim 8, wherein A is an electron acceptor selected from the group consisting of halo groups, nitro groups, cyano groups, carboxyl groups, carbonyl groups, and alkoxy carbonyl groups.

10. A nonlinear optical material, comprising a recrystallized crystalline bridged di-arene having a net macroscopic dipole moment and described by the formula:

$$D—Ar_1—E_1=N—N=E_2—Ar_2—A$$

wherein:
Ar$_1$ and Ar$_2$ are arenyl groups which may be the same or different and which are selected from the group consisting of mononuclear aryl groups, and conjugated di-nuclear aryl groups;
D is an electron donor substituent on the first aryl group;
A is an electron acceptor substituent on the second aryl group;
E$_1$ and E$_2$ are each independently substituted or unsubstituted methylene or ethylene groups which may be the same or different and which have substituent side groups which contain 1 or 2 carbon atoms and are in a racemic relationship,
said material having a macroscopic dipole alignment factor of at least 0.1.

11. The composition of claim 10, wherein said bridged di-arene is characterized by the formula:

$$D—\text{C}_6\text{H}_4—\underset{R'}{\overset{}{C}}=N—N=\underset{R''}{\overset{}{C}}—\text{C}_6\text{H}_4—A$$

wherein R' and R" are each independently a methyl or ethyl group.

12. The composition of claim 11, wherein R' and R" are racemic methyl groups.

13. The composition of claim 12, wherein D is an electron donor selected from the group consisting of ethers, thioethers, amines, alkylamines, dialkylamines and piperidines.

14. The composition of claim 13, wherein A is electron acceptor selected from the group consisting of halo groups, nitro groups, cyano groups, carboxyl groups, carbonyl groups, and alkoxy carbonyl groups.

15. The composition of claim 12, wherein D is a methoxy group and A is selected from the group consisting of Br, CN and NO$_2$.

16. The material of claim 10, wherein said crystalline diarene has a macroscopic dipole alignment factor of at least 0.5.

17. The material of claim 16, wherein said crystalline di-arene is 4-methoxy-4'-bromoacetophenone azine.

18. In a process for electro-optical modification of a beam of monochromatic electromagnetic radiation, the steps comprising:
a. providing a light-modifying cell containing a nonlinear optical material comprising a crystalline azine bridged di-arene having a macroscopic dipole alignment factor of at least 0.1 and described by the formula D—Ar$_1$—B—Ar$_2$—A;
wherein:
Ar$_1$ is a first arenyl group and Ar$_2$ is a second arenyl group which may be the same as or different from Ar$_1$;
D is an electron donor substituent on said first arenyl group;
A is an electron acceptor group on said second arenyl group; and
B is an azine bridge interconnecting said first and second arenyl groups;
said material having a macroscopic dipole alignment factor of at least 0.1;
b. applying a primary beam of monochromatic electromagnetic radiation to said modulating cell;
c. producing a secondary beam of monochromatic radiation from said cell having a modified electromagnetic characteristic in relation to the corresponding electromagnetic characteristic of the applied radiation beam; and
d. applying said secondary beam to a utilization system.

19. The process of claim 18, wherein the modified electromagnetic characteristic is a change in phase of the applied beam.

20. The process of claim 18, wherein the modified electromagnetic characteristic involves modulation of the applied beam to provide an amplitude modulation characteristic of the applied beam.

21. The process of claim 18, wherein said modified electromagnetic characteristic is the frequency of the applied beam.

22. The process of claim 21, wherein said light modifying cell comprises crystalline 4-methoxy-4'-bromoacetophenone azine which functions as a second harmonic generator which doubles the frequency of said primary beam to produce a second beam having a fundamental frequency twice that of the primary beam.

23. The process of claim 18, wherein said nonlinear optical material has a macroscopic dipole alignment factor of at least 0.5.

* * * * *